US008431626B2

(12) United States Patent
Bowman et al.

(10) Patent No.: US 8,431,626 B2
(45) Date of Patent: Apr. 30, 2013

(54) DISULFIDE MONOMERS COMPRISING ETHYLENICALLY UNSATURATED NORBORNYL GROUPS SUITABLE FOR DENTAL COMPOSITIONS

(75) Inventors: Christopher N. Bowman, Boulder, CO (US); Hee Young Park, Asan-si (KR); Christopher J. Kloxin, Newark, DE (US); Ahmed S. Abuelyaman, Woodbury, MN (US); Joel D. Oxman, Minneapolis, MN (US); Yizhong Wang, Woodbury, MN (US)

(73) Assignees: 3M Innovative Properties Company, St. Paul, MN (US); The Regents of the University of Colorado, Denver, CO (US)

(*) Notice: Subject to any disclaimer, the term of this patent is extended or adjusted under 35 U.S.C. 154(b) by 102 days.

(21) Appl. No.: 13/110,898

(22) Filed: May 18, 2011

(65) Prior Publication Data

US 2012/0295227 A1 Nov. 22, 2012

(51) Int. Cl.
- *A61K 6/083* (2006.01)
- *C07C 321/20* (2006.01)
- *C07C 321/16* (2006.01)
- *C08F 232/06* (2006.01)
- *C08F 236/20* (2006.01)

(52) U.S. Cl.
USPC ............. 523/115; 568/38; 568/57; 568/58; 433/228.1; 106/35; 526/281; 526/282

(58) Field of Classification Search ............. 523/115; 568/38, 57, 58; 433/228.1; 106/35; 526/281, 526/282
See application file for complete search history.

(56) References Cited

U.S. PATENT DOCUMENTS

| 4,503,169 | A  | 3/1985  | Randklev |
| 5,545,676 | A  | 8/1996  | Palazzotto |
| 6,030,606 | A  | 2/2000  | Holmes |
| 6,284,898 | B1 | 9/2001  | Moszner |
| 6,387,981 | B1 | 5/2002  | Zhang |
| 6,572,693 | B1 | 6/2003  | Wu |
| 6,730,156 | B1 | 5/2004  | Windisch |
| 6,794,520 | B1 | 9/2004  | Moszner |
| 7,090,721 | B2 | 8/2006  | Craig |
| 7,090,722 | B2 | 8/2006  | Budd |
| 7,156,911 | B2 | 1/2007  | Kangas |
| 7,241,437 | B2 | 7/2007  | Davidson |
| 7,605,190 | B2 | 10/2009 | Moszner |
| 7,649,029 | B2 | 1/2010  | Kolb |
| 7,674,850 | B2 | 3/2010  | Karim |
| 7,888,400 | B2 | 2/2011  | Abuelyaman |
| 7,943,680 | B2 | 5/2011  | Bowman |
| 2008/0194722 | A1 | 8/2008 | Abuelyaman |
| 2008/0269460 | A1* | 10/2008 | Bowman et al. ............ 528/364 |
| 2009/0270528 | A1* | 10/2009 | Bowman et al. ............ 523/116 |

FOREIGN PATENT DOCUMENTS

| WO | WO 01/30305   | 5/2001  |
| WO | WO 01/30307   | 5/2001  |
| WO | WO 03/063804  | 8/2003  |
| WO | WO 2007/146210 | 12/2007 |
| WO | WO 2008/082881 | 7/2008  |
| WO | WO 2009/080797 | 7/2009  |

OTHER PUBLICATIONS

Kloxin et al., "Stress Relaxation via Addition—Fragmentation Chain Transfer in a Thiol-ene Photopolymerization" Macromolecules 2009, 42, 2551-2556.
Lu et al., "Probing the origins and control of shrinkage stress in dental resin-composites: I. Shrinkage stress characterization technique", Jounral of Materials Science: Materials in Medicine 15 (2004) 1097-1103.
Lu et al., "Investigations of step-growth thiol-ene polymerizations for novel dental restoratives", Dental Materials (2005) 21, 1129-1136.
Park et al., "Covalent adaptable networks as dental restorative resins: Stress relaxation by addition-fragmentation chain transfer in allyl sulfide-containing resins", Dental Materials 26 (2010) 1010-1016.
Scott et al., "Actuation in Crosslinked Polymers via Photoinduced Stress Relaxation", Advanced Materials 2006, 18, 2128-2132.
Dolman et al., "Supported Chiral Mo-Based Complexes as Efficient Catalysts for Enantioselective Olefin Metathesis", J. Am. Chem. Soc. 2004, 126, 10945-10953.
Ganster et al., "New Photocleavable Structures. Diacylgermane-Based Photoinitiators for Visible Light Curing", Macromolecules 2008, 41, 2394-2400.
Watts, Determination of Polymerization Shrinkage Kinetics in Visible-Light-Cured Materials: Methods Development, Dental Materials (Oct. 1992) pp. 281-287.
Cara et al., "Influence of Bis-GMA Derivative Monomer-Based Particulate Composite Resins on the Cuspal Deformation and Microleakage of Restored Teeth" Particulate Science and Technology, 28: 191-206, (2010).
U.S. Appl. No. 13/169,306, filed Jun. 27, 2011.
U.S. Appl. No. 61/443,218, filed Feb. 15, 2011.
U.S. Appl. No. 61/521,134, filed Aug. 8, 2011.

* cited by examiner

*Primary Examiner* — Michael Pepitone
(74) *Attorney, Agent, or Firm* — Carolyn A. Fischer

(57) ABSTRACT

Dental compositions and disulfide monomers described. The disulfide monomer comprises a disulfide backbone group wherein each of the sulfur atoms are bonded to a group terminating with an ethylenically unsaturated norbornyl group; and at least one other monomer comprising at least two ethylenically unsaturated groups.

21 Claims, No Drawings

DISULFIDE MONOMERS COMPRISING ETHYLENICALLY UNSATURATED NORBORNYL GROUPS SUITABLE FOR DENTAL COMPOSITIONS

ACKNOWLEDGEMENT OF GOVERNMENT SUPPORT

This invention was made with government support under grant number DE010959 awarded by the National Institutes of Health. The government has certain rights in the invention.

SUMMARY

Although various hardenable dental compositions have been described, industry would find advantage in compositions having improved properties such as reduced stress and/or reduced shrinkage while maintaining sufficient mechanical properties and depth of cure.

In one embodiment, a dental composition is described comprising a disulfide monomer comprising a disulfide backbone group wherein each of the sulfur atoms are bonded to a group terminating with an ethylenically unsaturated norbornyl group; and at least one other monomer comprising at least two ethylenically unsaturated groups.

In some embodiments, the disulfide backbone group is an alkylene disulfide. In other embodiments, the disulfide backbone group is an allylic disulfide.

For embodiments wherein the dental composition is a dental restoration material, the dental composition comprises an inorganic oxide filler, such as silica nanoparticles, zirconia nanoparticles, or mixtures thereof.

In another embodiment, a method of treating a tooth surface is described comprising providing a hardenable dental composition the previously described ethylenically unsaturated norbornyl disulfide monomer; placing the dental composition on a tooth surface in the mouth of a subject; and hardening the hardenable dental composition.

In another embodiment, dental articles are described, comprising an at least partially hardened dental composition comprising the previously described ethylenically unsaturated norbornyl disulfide monomer.

In yet another embodiment, a method of treating a tooth surface is described comprising providing the at least partially hardened dental article just described, and adhering the dental article on a tooth surface in the mouth of a subject.

In other embodiments, a class of monomers is described having the structure

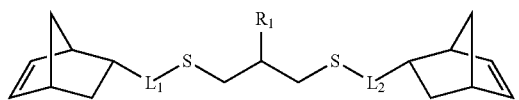

wherein $R_1$ is a hydrogen, a $C_1$-$C_4$ alkyl group, or methylene; and
L1 and L2 are independently divalent linking groups.

DETAILED DESCRIPTION

As used herein, "dental composition" refers to a material, optionally comprising filler, capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns, bridges, and articles for dental implants. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

As used herein:

"shrinkage" refers to the volumetric change as a result of curing, i.e. shrinkage that occurs after gelation as can be measured using the Watts Shrinkage (Watts) test method described in the examples. Hence, shrinkage does not refer to the volumetric change that occurs prior to gelation.

"dental article" refers to an article that can be adhered (e.g., bonded) to a tooth structure or dental implant. Dental articles include, for example, crowns, bridges, veneers, inlays, onlays, fillings, orthodontic appliances and devices.

"orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

"oral surface" refers to a soft or hard surface in the oral environment. Hard surfaces typically include tooth structure including, for example, natural and artificial tooth surfaces, bone, and the like.

"hardenable" and "curable" is descriptive of a material or composition that can be cured (e.g., polymerized or crosslinked) by heating to induce polymerization and/or crosslinking; irradiating with actinic irradiation to induce polymerization and/or crosslinking; and/or by mixing one or more components to induce polymerization and/or crosslinking "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

"hardened" refers to a material or composition that has been cured (e.g., polymerized or crosslinked).

"hardener" refers to something that initiates hardening of a resin. A hardener may include, for example, a polymerization initiator system, a photoinitiator system, a thermal initiator and/or a redox initiator system.

"(meth)acrylate" is a shorthand reference to acrylate, methacrylate, or combinations thereof "(meth)acrylic" is a shorthand reference to acrylic, methacrylic, or combinations thereof and "(meth)acryl" is a shorthand reference to acryl, methacryl, or combinations thereof.

"acryloyl" is used in a generic sense and mean not only derivatives of acrylic acid, but also amine, and alcohol derivatives, respectively;

"(meth)acryloyl" includes both acryloyl and methacryloyl groups; i.e. is inclusive of both esters and amides.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION

Presently described are dental compositions, dental articles, methods of use, and ethylenically unsaturated norbornyl disulfide monomers.

The monomer comprises a disulfide backbone group wherein each of the sulfur atoms are bonded to a group terminating with an ethylenically unsaturated norbornyl group. The ethylenically unsaturated norbornyl group is typically 1,3-norbornyl methylene (i.e. norbornene).

The disulfide backbone group and monomer is typically linear or branched. The disulfide backbone group is typically acyclic. The monomer has the general structure

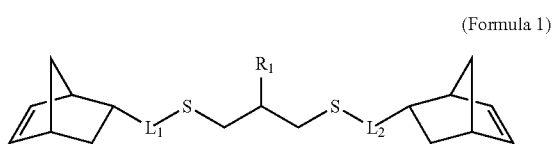

(Formula 1)

wherein $R_1$ is a hydrogen, a $C_1$-$C_4$ alkyl group, or methylene; and
L1 and L2 are independently divalent linking groups.

In some embodiments, L1 and L2 are independently a straight-chain, branched, or cyclic C1-C20 alkylene, arylene, or alkyarylene. In some embodiments, L1 and L2 have no greater than 8, 6, or 4 carbon atoms. In some embodiments, L1 and L2 further comprise at least one heteroatom, i.e. oxygen, nitrogen, or sulfur. Such oxygen or sulfur atom typically forms an ester, thioester, ether, or thioether linkage. Such nitrogen atom typically forms a urethane linkage. Thus, the linking group may comprise at least one moiety selected from ester, thioester, ether, thioether, urethane and combinations of such moieties.

In some embodiments, the divalent linking groups of the ethylenically unsaturated norbornyl disulfide monomers are typically sufficiently low in molecular weight such that the monomer is a stable liquid at 25° C. In other embodiments, the ethylenically unsaturated norbornyl disulfide monomers are solids at 25° C. that can be dissolved or dispersed in the other ethylenically unsaturated monomer(s).

Increasing the molecular weight without forming a solid at 25° C. can be achieved by various synthetic approaches. In some embodiments, the linking groups have one or more pendant substituents. For example, the linking groups may comprise one or more hydroxyl group substituents such an in the case of linking groups comprising alkoxy segments. In other embodiments, the linking groups are branched, and/or comprise at least one (i.e. aliphatic) cyclic moiety, and/or comprise at least one aromatic moiety.

The some embodiments, the disulfide backbone group or entire backbone of the monomer is free of ethylenically unsaturated groups. Thus, the norbornene end groups are the sole ethylenically unsaturated groups of the monomer. In this embodiment, the disulfide backbone group is typically an alkylene disulfide. One favored species is

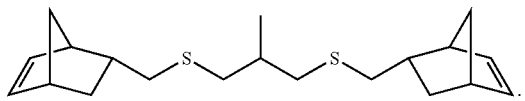 [SMILES: CC(CSCC1CC2C=CC1C2)CSCC1CC2C=CC1C2]

Unexpectedly, such disulfide monomers were found to provide lower shrinkage than (meth)acrylate monomer having a cyclic allylic sulfide moiety, as described in US2008/0194722.

In favored embodiments, the disulfide backbone group comprises a pendant ethylenically unsaturated group, such as methylene. In this embodiment, the disulfide backbone group is typically an allylic disulfide. Due to the ethylenic unsaturation, this class of monomers can be characterized as addition-fragmentation agents that are free-radically cleavable. One favored species is

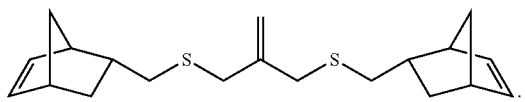 [SMILES: C=C(CSCC1CC2C=CC1C2)CSCC1CC2C=CC1C2]

Such disulfide monomers having pendant ethylenic unsaturation were found to provide lower shrinkage and less stress than the alkylene disulfide norbornene monomers, i.e. those lacking pendant ethylenic unsaturation as described herein.

An allylic disulfide ether dicarboxylic acid intermediate can be made from commercially available 3-chloro-2-chloromethyl-1-propene and a mercapto carboxylic acid such as 2-mercaptoacetic acid or 2-mercaptoprionic. Other suitable thiol-bearing compounds can be utilized providing other linking groups. Mercapto carboxylic acids can be reacted with 2 equivalents of NaOH in excess ethanol. After complete dissolution of NaOH and the acid in ethanol, 3-cholor-3-chloromethyl-1-propene can be added slowly to the continuously stirred solution. After complete addition, the mixture is refluxed for additional 30 minutes then cooled to room temperature. The solvent can be removed using a rotatory evaporator followed by dissolving the residue in an acidic solution such as 1 N HCl. Extraction with an organic solvent followed by drying the organic layer then concentrating it in a rotary evaporator will give the allylic disulfide dicarboxylic acid intermediate.

The allylic disulfide dicarboxylic acid intermediate can be reacted with brominated norbornene compounds, such as 5-bromomethyl-norbornene, following a method that describes the reaction of 5-bromomethyl norbonene and carboxylic acids as described in WO2009/80797. An illustrative reactive scheme is as follows:

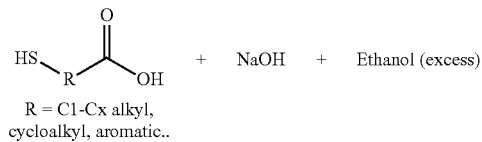

R = C1-Cx alkyl, cycloalkyl, aromatic..

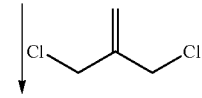

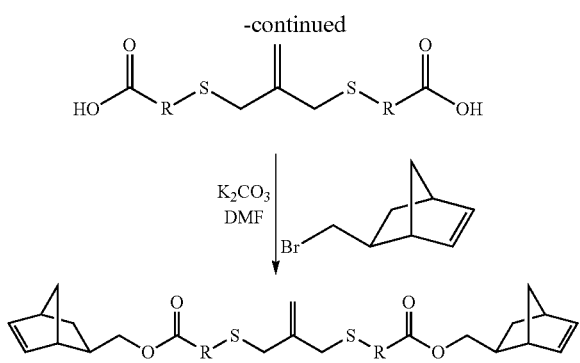

When a single disulfide dicarboxylic acid and a single norbornene compound are reacted, L1 and L2 are typically the same. However, when more than one disulfide dicarboxylic acid or norbornene compound are utilized, a statistical distribution of compounds are formed wherein L2 and L2 can be different.

In one embodiment, disulfide norbornene monomers described herein were prepared by reacting 1,3-dicyclopentadiene with allyl bromide to form 5-bromomethyl norbornene. The 5-bromomethyl norbornene is then reacted with 3-mercapto-2-(mercaptomethyl)-1-propene or and 1,3-dimercapto-2-methylpropane. In this particular reaction sequence, the divalent linking group ($L_1$ and $L_2$ of Formula 1) is —$CH_2$—.

The ethylenically unsaturated norbornyl disulfide monomers, such as those having ethylenic unsaturation in the backbone, suitable for use as addition-fragmentation materials ("AFM"), may be added to a dental composition comprising at least one ethylenically unsaturated monomer or oligomer. Without intending to be bound by theory, it is surmised that the inclusion of such addition-fragmentation material reduces the polymerization-induced stresses, such as by the mechanism described in U.S. provisional patent application 61/442,980. Since such ethylenically unsaturated norbornyl disulfide monomers comprise at least two ethylenically unsaturated groups, such monomer can function as crosslinking agents, where the crosslinks are labile.

The concentration of a component of hardenable (i.e. polymerizable) dental composition described herein can be expressed with respect to the (i.e. unfilled) polymerizable resin portion of the dental composition. For favored embodiments, wherein the composition further comprises filler, the concentration of monomer can also be expressed with respect to the total (i.e. filled) composition. When the composition is free of filler, the polymerizable resin portion is the same as the total composition.

The polymerizable resin portion of the hardenable dental composition described herein comprise at least 0.5 wt-%, or 1 wt-%, 1.5 wt-%, or 2 wt-% of one or more of the ethylenically unsaturated norbornyl disulfide monomers described herein. The polymerizable resin portion of the hardenable dental composition may comprise a single ethylenically unsaturated norbornyl disulfide monomer, as described herein, or a combination of two or more. In some embodiments, at least one of the norbornyl sulfide monomers functions as an addition-fragmentation agent. The total amount of (e.g. addition-fragmentation agent) norbornyl sulfide monomers in the polymerizable resin portion of the hardenable dental composition is typically no greater than 40 wt-%, 35 wt-%, 25 wt-%, or 20 wt-%. As the concentration of the (e.g. addition-fragmentation) norbornyl sulfide monomer increases, the stress and Watts Shrinkage typically decrease. However, when the amount of (e.g. addition-fragmentation) norbornyl sulfide monomer exceeds an optimal amount, mechanical properties such as Diametral tensile strength and/or Barcol hardness, or depth of cure may be insufficient.

Materials with high polymerization stress upon curing generate strain in the tooth structure. One clinical consequence of such stress can be a decrease in the longevity of the restoration. The stress present in the composite passes through the adhesive interface to the tooth structure generating cuspal deflection and cracks in the surrounding dentin and enamel which can lead to postoperative sensitivity as described in R. R. Cara et al, Particulate Science and Technology 28; 191-206 (2010). Preferred filled dental compositions (useful for restorations such as fillings and crowns) described herein typically exhibits a shrinkage stress, as measured using tensometry (according to the test method described in the examples) of no greater than 550 Kpa and in favored embodiments no greater than 500 Kpa, or 450 Kpa. In some embodiments, the shrinkage stress is no greater than 400 Kpa. Preferred unfilled dental compositions described herein typically exhibits a shrinkage stress, as measured using tensometry (according to the test method described in the examples) of no greater than 2000 Kpa, or 1500 Kpa, or 1000 Kpa, and in favored embodiments no greater than 500 KPa, or 400 Kpa, or 300 Kpa. In some embodiments, the shrinkage stress is no greater than 200 Kpa.

The filled hardenable (i.e. polymerizable) dental composition described herein typically comprises at least 0.5 wt-%, or 1 wt-%, or 2 wt-% of (e.g. addition-fragmentation agent) ethylenically unsaturated norbornyl disulfide monomer(s). The total amount of (e.g. addition-fragmentation agent) norbornyl disulfide monomer(s) in the filled hardenable (i.e. polymerizable) dental composition is typically no greater than 10 wt-%, or 9 wt-%, or 8 wt-%, or 7 wt-%.

The hardenable (e.g. dental) compositions described herein further comprise at least one ethylenically unsaturated monomer or oligomer in combination with the (e.g. addition-fragmentation agent) ethylenically unsaturated norbornyl disulfide monomer(s), as described herein. In some embodiments, such as primers, the ethylenically unsaturated monomer may be monofunctional, having a single (e.g. terminal) ethylenically unsaturated group. In other embodiments, such as dental restorations the dental composition comprises one or more multifunctional ethylenically unsaturated monomers. The phrase "multifunctional ethylenically unsaturated" means that the monomers each comprise at least two ethylenically unsaturated (e.g. free radically) polymerizable groups.

In favored embodiments, such ethylenically unsaturated group is a (e.g. terminal) free radically polymerizable group including (meth)acryl such as (meth)acrylamide ($H_2C$=CHCON— and $H_2C$=CH($CH_3$)CON—) and (meth)acrylate ($CH_2$CHCOO— and $CH_2C$ ($CH_3$)COO—). Other ethylenically unsaturated polymerizable groups include vinyl ($H_2C$=C—) including vinyl ethers ($H_2C$=CHOCH—). The ethylenically unsaturated terminal polymerizable group(s) is preferably a (meth)acrylate group, particularly for compositions that are hardened by exposure to actinic (e.g. UV) radiation. Further, methacrylate functionality is typically preferred over the acrylate functionality in curable dental compositions.

The ethylenically unsaturated monomer may comprise various ethylenically unsaturated monomers, as known in the art, for use in dental compositions.

In favored embodiments, the (e.g. dental) composition comprises one or more ethylenically unsaturated (e.g. (meth)acrylate) monomers having a low volume shrinkage monomer. Preferred (e.g. filled) dental compositions (useful for restorations such as fillings and crowns) described herein comprise one or more low volume shrinkage monomers such that the composition exhibits a Watts Shrinkage of less than about 2%. In some embodiments, the Watts Shrinkage is no greater than 1.90%, or no greater than 1.80%, or no greater than 1.70%, or no greater than 1.60%. In favored embodiments, the Watts Shrinkage is no greater than 1.50%, or no greater than 1.40%, or no greater than 1.30%.

Preferred low volume shrinkage monomers include cyclic allylic sulfide moiety such as described in US2008/0194722; methylene dithiepane silanes as described in U.S. Pat. No. 6,794,520; oxetane silanes such as described in U.S. Pat. No. 6,284,898; and branched multi(meth)acrylate monomers, such as di-, tri, and/or tetr-(meth)acryloyl-containing materials described in WO2008/082881; each of which are incorporated herein by reference.

In some embodiments, the dental composition comprises a polymerizable compound having at least one cyclic allylic sulfide moiety with at least one (meth)acryloyl moiety.

Such a polymerizable compound is referred to herein as a hybrid monomer or a hybrid compound. The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, $SO_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have two or more cyclic allylic sulfide moieties. The (meth)acryloyl moiety is preferably a (meth)acryloyloxy (i.e. a (meth) acrylate moiety) or a (meth)acryloylamino (i.e., a (meth) acrylamide moiety).

In one embodiment, the low shrinkage monomer includes those represented by the formulae:

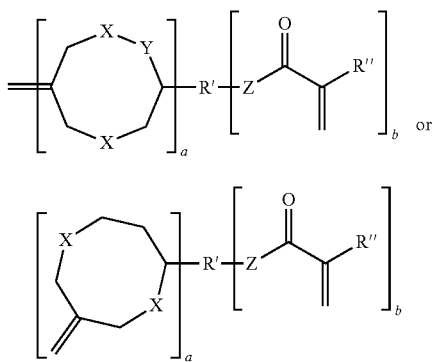

Formula 1a

Formula 1b

In the above formulae, each X can be independently selected from S, O, N, C (e.g., $CH_2$ or CRR, where each R is independently a H or an organic group), SO, $SO_2$, N-alkyl, N-acyl, NH, N-aryl, carboxyl or carbonyl group, provided that at least one X is S or a group comprising S. Preferably, each X is S.

Y is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with Y thus being either absent or methylene, respectively. In some embodiments, Y is either absent or is a C1 to C3 alkylene, optionally including a heteroatom, carbonyl, acyl, or combinations thereof.

Z is O, NH, N-alkyl (straight chain or branched), or N-aryl (phenyl or substituted phenyl).

The R' group represents a linker selected from alkylene (typically having more than one carbon atom, i.e. excluding methylene), alkylene optionally including a heteroatom (e.g., O, N, S, S—S, SO, SO2), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, alkylthio, carbonyl, acyl, acyloxy, amido, urethane group, urea group, a cyclic allylic sulfide moiety, or combinations thereof.

R" is selected from H, and $CH_3$, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, alkylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

A typical low shrinkage monomer can comprise an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

Representative polymerizable compounds having at least one cyclic allylic sulfide moiety with at least one (meth) acryloyl moiety include the following

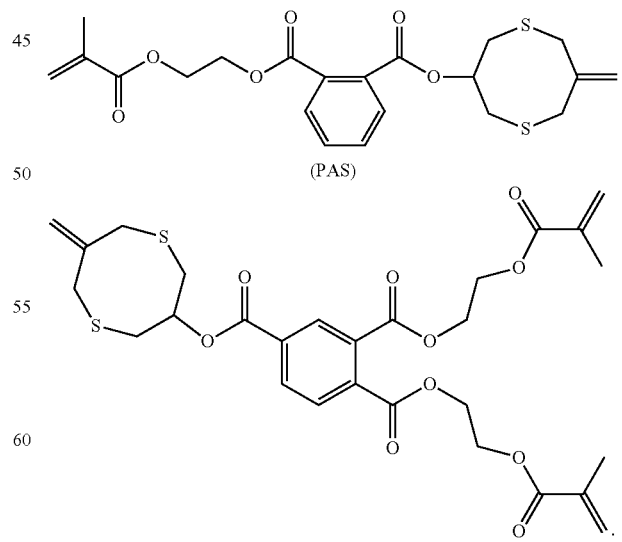

(PAS)

In another embodiment, the dental composition comprises a branched multi(meth)acrylate low shrinkage monomer that includes at least one di-, tri-, and/or tetra (meth)acryloyl-containing materials having the general formula:

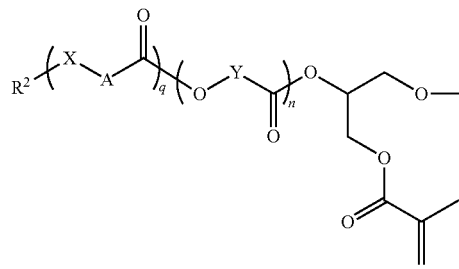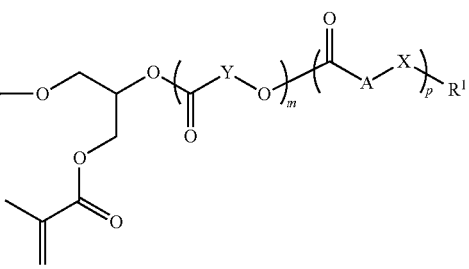

wherein: each X independently represents an oxygen atom (O) or a nitrogen atom (N); Y and A each independently represent an organic group, and $R^1$ represents —C(O)C(CH$_3$)=CH$_2$, and/or (ii) q=0 and $R^2$ represents —C(O)C(CH$_3$)=CH$_2$; m=1 to 5; n=0 to 5; p and q are independently 0 or 1; and $R^1$ and $R^2$ each independently represent H, —C(O)CH=CH$_2$, or —C(O)C(CH$_3$)=CH$_2$. In some embodiments, Y does not represent —NHCH$_2$CH$_2$-when p=0. Although, this material is a derivative of bisphenol A, when other low volume shrinkage monomer are employed, the dental composition is free of (meth)acrylate monomers derived from bisphenol.

In favored embodiments, the majority of the (e.g. unfilled) polymerizable resin composition comprises one or more low volume shrinkage monomers. For example, at least 50%, 60%, 70%, 80%, 90%, and even 100% of the (e.g. unfilled) polymerizable resin may comprises low volume shrinkage monomer(s), at least one being the sulfide norbornene monomer(s) described herein.

In this embodiment, the (unfilled) polymerizable resin may comprise a small concentration of other monomer(s). By "other" is it meant an ethylenically unsaturated monomer such as a (meth)acrylate monomer that is not a low volume shrinkage monomer.

The concentration of such other monomer(s) is typically no greater than 20 wt-%, 19 wt-%, 18 wt-%, 17 wt-%, 16 wt-%, or 15 wt-% of the (unfilled) polymerizable resin portion. The concentration of such other monomers is typically no greater than 5 wt-%, 4 wt-%, 3 wt-%, or 2 wt-% of the filled polymerizable dental composition.

Although the inclusion of an addition fragmentation agent in a low volume shrinkage resin composition typically provides the lowest stress and/or lowest shrinkage, the ethylenically unsaturated norbornyl monomers, particularly those that function as addition-fragmentation agents, can also reduce the stress and shrinkage of dental compositions comprising conventional dental (meth)acrylate monomers. In this embodiment, the (unfilled) polymerizable dental composition may comprise one or more conventional dental monomers in combination with at least one the ethylenically unsaturated norbornyl monomer(s) within the concentration ranges previously described. In this embodiment, the remainder of the (unfilled) polymerizable dental composition may comprise one or more conventional (meth)acrylate monomers (in the absence of low shrinkage monomers).

Typical conventional (e.g. "other") hardenable (meth)acrylate monomers include for example ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylglycol dimethacrylate (NPGDMA), and polyethyleneglycol dimethacrylate (PEGDMMA).

The curable component of the curable dental composition can include a wide variety of other ethylenically unsaturated compounds (with or without acid functionality), epoxy-functional (meth)acrylate resins, vinyl ethers, and the like.

The (e.g., photopolymerizable) dental compositions may include free radically polymerizable monomers, oligomers, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-, di- or poly-(meth)acrylates (i.e., acrylates and methacrylates).

The ethylenically unsaturated monomers of the dental composition are typically stable liquids at about 25° C. meaning that the monomer do not substantially polymerize, crystallize, or otherwise solidify when stored at room temperature (about 25° C.) for a typical shelf life of at least 30, 60, or 90 days. The viscosity of the monomers typically does not change (e.g. increase) by more than 10% of the initial viscosity.

Particularly for dental restoration compositions, the ethylenically unsaturated monomers generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight monomer lacking such substituents).

An initiator is typically added to the mixture of polymerizable ingredients. The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

The addition-fragmentation agent is generally free-radically cleavable. Although photopolymerization is one mechanism for generating free radicals, other curing mechanisms also generate free radicals. Thus, the addition-fragmentation agent does not require irradiation with actinic radiation (e.g. photocuring) in order to provide the reduction in stress during curing.

In some embodiments, the mixture of monomers is photopolymerizable and the composition contains a photoinitiator (i.e., a photoinitiator system) that upon irradiation with actinic radiation initiates the polymerization (or hardening)

of the composition. Such photopolymerizable compositions can be free-radically polymerizable. The photoinitiator typically has a functional wavelength range from about 250 nm to about 800 nm. Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays. For this embodiment, suitable photoinitiators include those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

In some embodiments, the photoinitiator comprises at least one acyl germanium compound, such as described in U.S. Pat. No. 7,605,190. In some embodiments, such photoinitiator has been found to provide higher polymerization of the norbornene group (i.e. less unreacted norbornene group after photocuring.

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The dental compositions comprising the multifunctional ethylenically unsaturated monomers may be chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

In favored embodiments, such as when the dental composition is employed as a dental restorative (e.g. dental filling or crown) or an orthodontic cement, the dental composition typically comprises appreciable amounts of (e.g. nanoparticle) filler. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

The (e.g. filled) dental composite materials typically exhibit a Diametral Tensile Strength (DTS) of at least about 50, 55, 60, 65 and preferably at least 70 MPa or greater. The depth of cure is typically at least 3 and preferably at least 3.5, 4, or greater and comparable to commercially available (e.g. filled) dental compositions suitable for restorations.

The glass transition temperature (Tg) of a filled or unfilled dental composition is typically greater than 50° C. or 60° C. By inclusion of an ethylenically unsaturated norbornyl disulfide monomer, particularly in combination with other low shrinkage monomer, the Tg may be lower than a comparative dental composition (based on BisGMA and TEGDMA). For example, the Tg of an unfilled dental composition may be less than 150° C., 125° C., or 100° C. Further, the Tg of a filled dental composition may be less than 200° C., 175° C., or 150° C. The elastic modulus (E') at 0° C. of an unfilled dental composition may range from about 1.5 to about 3.5 GPa. The elastic modulus (E') at 0° C. of a filled dental composition may range from about 10 to about 15 GPa. The flexural modulus of a filled dental composition is typically at least 5000 Mpa, and preferably at least 10,000 to 15,000 Mps. The flexural strength of a filled dental composition is typically at least 70, 75, or 80 Mpa.

Dental compositions suitable for use as dental adhesives can optionally also include filler in an amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Non-acid-reactive inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. Nos. 6,387,981 (Zhang et al.) and 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. Nos. 7,090,721 (Craig et al.), 7,090,722 (Budd et al.) and 7,156,911; and U.S. Pat. No. 7,649,029 (Kolb et al.).

Examples of suitable organic filler particles include filled or unfilled pulverized polycarbonates, polyepoxides, poly (meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO 1041.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin. Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formulas: $CH_2=C(CH_3)_mSi(OR)_n$ or $CH_2=C(CH_3)_nC=OOASi(OR)_n$; wherein m is 0 or 1, R is an alkyl group having 1 to 4 carbon atoms, A is a divalent organic linking group, and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependant upon several factors such as particle size, particle type, modifier molecular wt, and modifier type. In general it is preferred that approximately a monolayer of modifier is attached to the surface of the particle.

If desired, the compositions can contain additives such as indicators, dyes, pigments, inhibitors, accelerators, viscosity modifiers, wetting agents, buffering agents, radical and cationic stabilizers (for example BHT), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. In some embodiments, a dental adhesive may be applied prior to application of the curable dental restoration material described herein. Dental adhesives are also typically hardened by curing concurrently with curing the highly filled dental restoration composition. The method of treating an oral surface may comprise providing a dental article and adhering the dental article to an oral (e.g. tooth) surface.

In other embodiments, the compositions can be hardened (e.g., polymerized) into dental articles prior to applying. For example, a dental article such as a crown may be pre-formed from the hardenable dental composition described herein. Dental composite (e.g. crowns) articles can be made from the curable composition described herein by casting the curable composition in contact with a mold and curing the composition. Alternatively, dental composite (e.g. crowns) article can be made by first curing the composition forming a mill blank and then mechanically milling the composition into the desired article.

Another method of treating a tooth surface comprises providing a dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in U.S. Pat. No. 7,674,850 (Karim et al.); incorporated herein by reference.

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

UDMA (Diurethane dimethacrylate, CAS No. 41137-60-4, commercially available as Rohamere 6661-0, Rohm Tech, Inc., Malden, Mass.)
BisEMA6 (ethoxylated bisphenol A methacrylate as further described in U.S. Pat. No. 6,030,606, available as "CD541" from Sartomer, Exton, Pa.)
BisGMA (2,2-bis[4-(2-hydroxy-3-methacryloyloxypropoxy)phenyl]propane (Sigma Aldrich, St. Louis, Mo.)
TEGDMA (triethyleneglycol dimethacrylate, Sartomer Co., Inc., Exton, Pa.)
TrisMAP (Prepared as described in Example 2, WO 2008/082881, having a calculated molecular weight of 1131 g/mole.)
PAS (Prepared as described in U.S. Pat. No. 7,888,400, Example 1)
BHT (butylated hydroxytoluene, Sigma Aldrich)
Photoinitiators
CPQ (camphorquinone, Sigma Aldrich, St. Louis, Mo.)
EDMAB (ethyl 4-(N,N-dimethylamino)benzoate, Sigma Aldrich)
DPIHFP (diphenyl iodonium hexafluorophosphate, Alpha Aesar, Ward Hill, Mass.)
BAPO a phosphine oxide photoinitiator, available from BASF under the trade designation "Irgacure 819".
Ge-based photoinitiator (Dibenzoyl diethyl germane, synthesized) was prepared by a synthesis from diethyldi(2-phenyl-1,3-dithian-2-yl)germane, $CaCO_3$, and iodine following a procedure described in Beate Ganster, Urs Karl Fischer, Norbert Moszner, and Robert Liska; "New Photocleavable Structures. Diacylgermane-Based Photoinitiators for Visible Light Curing" *Macromolecules* 2008, 41, 2394-2400.
Zr/Si Nano-Cluster Filler (silane-treated zirconia/silica nanocluster filler prepared essentially as described in U.S. Pat. No. 6,730,156 (Preparatory Example A (line 51-64) and Example B (column 25 line 65 through column 26 line 40))
20 nm Silica Filler (silane-treated nano-sized silica having a nominal particle size of approximately 20 nanometers, prepared essentially as described in U.S. Pat. No. 6,572,693 B1, (column 21, lines 63-67 for Nanosized particle filler, Type #2))

Preparatory Examples 2-methyl-propane-1,3-di(norbornylmethylene sulfide) [MeDNS]

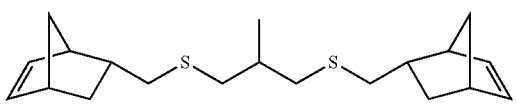

2-methylene-propane-1,3-di(norbornylmethylene sulfide) [MDNS]

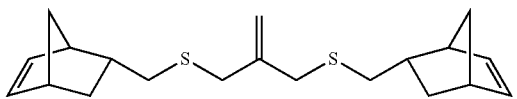 [SMILES: CC(CSCC1CC2C=CC1C2)CSCC1CC2C=CC1C2]

MDNS and MeDNS were synthesized from 5-bromomethyl norbornene with 3-mercapto-2-(mercaptomethyl)-1-propene and 1,3-dimercapto-2-methylpropane, respectively, according to the method described in Kloxin C J, Scott T F, Bowman C N. (2009) "Stress Relaxation Via Addition-Fragmentation Chain Transfer in a Thiol-Ene Photopolymerization." *Macromolecules* 42(7): 2551-6. PMCID: 20160931. The waxy/hazy solid (MDNS) and viscous/colorless liquid (MeDNS) were received after purification. To synthesize 5-bromomethyl norbornene, a reaction of 1,3-dicyclopentadiene with allyl bromide was performed in a pressure vessel heated at 170° C. for 12 hours. It was distilled at 175° C. at 1 atmosphere pressure before use. Such synthesis is described in Dolman S J, Hultzsch K C, Pezet F, Teng X, Hoveyda A H, Schrock R R. (2004) "Supported Chiral Mo-Based Complexes as Efficient Catalysts for Enantioselective Olefin Metathesis." *Journal of the American Chemical Society* 126(35): 10945-53. (See compound 48).

Test Methods
Watts Shrinkage Test Method
The Watts Shrinkage (Watts) Test Method measures shrinkage of a test sample in terms of volumetric change after curing, i.e. shrinkage that occurs after gelation. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. The results are reported as negative % shrinkage.

Diametral tensile strength (DTS) Test Method
Diametral tensile strength of a test sample was measured according to the following procedure. An uncured composite sample was injected into a 4-mm (inside diameter) glass tube; the tube was capped with silicone rubber plugs. The tube was compressed axially at approximately 2.88 kg/cm² pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany). The sample was cut with a diamond saw to form disks about 2 mm thick, which were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Samples were prepared and measured with results reported in MPa as the average of multiple measurements.

Depth of Cure Test Method
The depth of cure was determined by filling a 10 millimeter stainless steel mold cavity with the composite, covering the top and bottom of the mold with sheets of polyester film, pressing the sheets to provide a leveled composition surface, placing the filled mold on a white background surface, irradiating the dental composition for 20 seconds using a dental curing light (3M Dental Products Curing Light 2500 or 3M ESPE Elipar FreeLight2, 3M ESPE Dental Products), separating the polyester films from each side of the mold, gently removing (by scraping) materials from the bottom of the sample (i.e., the side that was not irradiated with the dental curing light), and measuring the thickness of the remaining material in the mold. The reported depths are the actual cured thickness in millimeters divided by 2.

Functional Group Conversion
The vinyl functional group conversion in each resin was determined using Fourier transform infrared (FTIR) spectroscopy (Nicolet 750) during photopolymerization. Samples (50 μm thickness) were irradiated for 5 minute at 10 mW/cm² intensity by two visible-light dental lamps (G-light equipped with a 470 nm band-pass filter (GC America Inc.) and 430 nm dental LED light (MODEL 5560 ALZ, 3M)). The conversions of the methacrylate, norbornene, and allyl sulfide were determined by monitoring infrared absorption peaks centered at 3105 cm$^{-1}$ (C=C—H stretching), 3058 cm$^{-1}$ (C=C—H stretching), and 3077 cm$^{-1}$ (C=C—H stretching), respectively. Gaussian fitting was used to deconvolute the peak areas as the methacrylate peak is overlapped with the norbornene and allyl sulfide peaks. (See Kloxin, C. J.; Scott, T. F.; Bowman, C. N.; *Macromolecules* 2009, 42, 2551-2556. and Park, H. Y.; Kloxin, C. J.; Scott, T. F.; Bowman, C. N. *Dental Materials* 2010, 26, 1010-1016.)

Shrinkage stress was monitored using tensometry during the photopolymerization of each resin or composite. Samples 6 mm in diameter and 1 mm thick were irradiated for 5 minutes at 10 mW/cm$^2$ intensity using the G-light dental lamp (equipped with a 470 nm filter). (See Lu, H.; Carioscia, J. A.; Stansbury, J. W.; Bowman, C. N. *Dental Materials* 2005, 21, 1129-1136 and Lu, H.; Stansbury, J. W.; Dickens, S. H.; Eichmiller, F. C.; Bowman, C. N. *Journal of Materials Science—Materials in Medicine* 2004, 15, 1097-1103.

Elastic moduli (E') and glass transition temperatures ($T_g$) of polymerized samples were determined by dynamic mechanical analysis (DMA) (TA Instruments Q800). Rectangular samples (length*width*thickness: ~8 mm*5 mm*1 mm) were prepared by sandwiching the material between 2 glass slides with 1 mm thickness spacer and cured under same irradiation conditions as used in the tensometer experiments. Experiments were performed at a strain and frequency of 0.1% and 1 Hz, respectively, and scanning the temperature twice at ramp rate of 1° C./minute. The $T_g$ was assigned as the temperature at tan delta peak maximum of the second scan.

Flexural strength and modulus were measured with a 858 Mini Bionix II Test System using a 3-point bending test procedure with 20 mm span and 1 mm/minute rate. For these tests, 2 mm samples were prepared by the same method as described for the DMA preparation.

TABLE 1

Dental Restoration Compositions
Percentages are % by weight

| Example | Example 1 | Example 2 | Example 3 |
|---|---|---|---|
| TrisMAP | 16.14% | 15.57% | 15.85% |
| BisEMA-6 | 3.44% | 3.31% | 3.37% |
| UDMA | 2.41% | 2.32% | 2.36% |
| PAS | 5.49% | | |
| MDNS | | | 5.40% |
| MeDNS | | 5.30% | |
| CPQ | 0.06% | 0.06% | 0.06% |
| EDMAB | 0.28% | 0.27% | 0.28% |
| DPIHFP | 0.14% | 0.14% | 0.14% |
| BHT | 0.04% | 0.04% | 0.04% |

TABLE 1-continued

Dental Restoration Compositions
Percentages are % by weight

| Example | Example 1 | Example 2 | Example 3 |
|---|---|---|---|
| Zr/Si Nano-Cluster | 65.16% | 66.07% | 65.61% |
| 20 nm Silica | 6.84% | 6.94% | 6.89% |

TABLE 2

Test Results

| | Example 1 | Example 2 | Example 3 | Control* |
|---|---|---|---|---|
| Watts Average (negative %) | 1.55 | 1.31 | 1.41 | 1.99 |
| Std Dev | 0.01 | 0.04 | 0.02 | 0.02 |
| Depth of cure - 2500 Curing Light (mm) | 3.52 | 2.79 | 3.00 | 3.92 |
| Std Dev | 0.08 | 0.16 | 0.11 | 0.2 |
| Depth of Cure, FreeLight2 (mm | 4.03 | 3.20 | 3.48 | 4.61 |
| Std Dev | 0.11 | 0.06 | 0.1 | 0.12 |
| Diametral Tensile Test (MPa) | 69.05 | 52.95 | 55.69 | 78.52 |
| Std Dev | 2.25 | 10.5 | 11.62 | 3.46 |

*Commercially available dental restoration material.

Various resin system blends were evaluations with two different types of photoinitiators and irradiation wavelengths. The test results are depicted in Table 3.

Various other properties of the cured resin systems were evaluated. Each of the resin systems contained 3 wt-% of the Ge-based photoinitiator Composites were made from these resin systems by combining 25 wt-% of the polymerizable organic portion with 75 wt-% of a dental filler as described in Example 1 of U.S. Pat. No. 4,503,169. The test results are depicted in Table 4.

TABLE 3

| Resin System | Irradiation wavelength/ photoinitiator (wt-%) | Functional group conversion [%] | | |
|---|---|---|---|---|
| | | Methacylate | Norbornene | Allyl sulfide |
| MeDNS/PAS (1:1) | 470 nm/ Ge-based (3 wt-%) | 100 (1) | 25 (2) | 5 (1) |
| MDNS/PAS (1:1) | | 97 (1) | 23 (2) | 2 (1) |
| MDN/PAS (1:4) | | 71 (1) | 41 (1) | 4 (1) |
| MeDNS/PAS (1:1) | 470 nm/ BAPO (3 wt-%) | 83 (1) | 9 (1) | 4 (1) |
| MDNS/PAS (1:1) | | 60 (1) | 5 (1) | 3 (1) |
| MeDNS/PAS (1:1) | 430 nm/ BAPO (3 wt-%) | 98 (1) | 11 (1) | 6 (1) |
| MDNS/PAS (1:1) | | 83 (1) | 9 (1) | 2 (1) |

TABLE 4

| Resin System | Stress [KPa] | Compliance of the tensometer | $T_g$ [° C.] | E' at 0° C. [GPa] | Flexural modulus [MPa] | Flexural strength [MPa] |
|---|---|---|---|---|---|---|
| MeDNS/PAS (1:1) | 250 (20) | A | 70 | 1.7 | — | — |
| MDNS/PAS (1:1) | 130 (20) | A | 55 | 2.2 | — | — |
| Comparative Resin BisGMA/TEGDMA 70/30 wt % | 2900 (300) | C | 160 | 3.5 | — | — |
| Composite MDNS PAS (1:1) | 370 (30) | B | 65 | 13 | 6300 (800) | 53 (4) |
| Composite MDNS PAS (1:2) | 400 (10) | B | 90 | 14 | 13500 (1000) | 92 (20) |

TABLE 4-continued

| Resin System | Stress [KPa] | Compliance of the tensometer | $T_g$ [° C.] | E' at 0° C. [GPa] | Flexural modulus [MPa] | Flexural strength [MPa] |
|---|---|---|---|---|---|---|
| Composite MDNS PAS (1:4) | 420 (30) | B | 110 | 13 | 14500 (500) | 87 (8) |
| Composite BisGMA/TEGMA 70/30 wt % | 640 (20) | B | 210 | 13 | 15300 (1000) | 118 (20) |

What is claimed is:

1. A dental composition comprising:
a disulfide monomer comprising a disulfide backbone group wherein each of the sulfur atoms are bonded to a group terminating with an ethylenically unsaturated norbornyl group and the disulfide backbone group lacks ethylenic unsaturation or has the structure

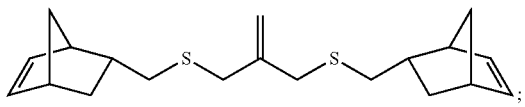 [SMILES: C=C(CSCC1CC2C=CC1C2)CSCC1CC2C=CC1C2]

and
at least one other ethylenically unsaturated monomer.

2. The dental composition of claim 1 wherein the disulfide backbone group is acyclic.

3. The dental composition of claim 1 wherein the ethylenically unsaturated norbornyl group is 1,3-norbornyl methylene.

4. The dental composition of claim 3 wherein the disulfide monomer comprises

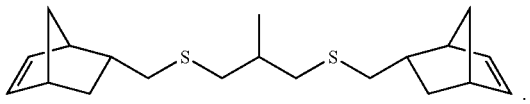 [SMILES: CC(CSCC1CC2C=CC1C2)CSCC1CC2C=CC1C2]

5. The dental composition of claim 1 wherein the ethylenically unsaturated groups of the other monomer are (meth)acrylate groups.

6. The dental composition of claim 1 wherein the other monomer is an aromatic monomer having a refractive index of at least 1.50.

7. The dental composition of claim 1 wherein the other monomer has a molecular weight (Mw) ranging from about 600 to 1500 g/mole.

8. The dental composition of claim 1 wherein the other monomer is a branched multi(meth)acrylate aromatic monomer, a monomer comprising a cyclic allylic sulfide moiety and at least one (meth)acryloyl moiety, or a mixture thereof.

9. The dental composition of claim 1 wherein the other monomer is selected from ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylglycol dimethacrylate (NPGDMA), polyethyleneglycol dimethacrylate (PEGDMA), and mixtures thereof.

10. The dental composition of claim 1 wherein the dental composition comprises inorganic oxide filler.

11. The dental composition of claim 10 wherein the inorganic oxide filler comprises silica nanoparticles, zirconia nanoparticles, or mixtures thereof.

12. The dental composition of claim 11 wherein the inorganic nanoparticles are in the form of nanoclusters.

13. The dental composition of claim 1 wherein the composition further comprises a free radical initiator.

14. The dental composition of claim 13 wherein the free radical initiator is a photoinitiator.

15. A method of treating a tooth surface, the method comprising
providing a hardenable dental composition according to claim 1;
placing the dental composition on a tooth surface of a subject; and
hardening the hardenable dental composition.

16. The method of claim 15 wherein the dental composition further comprises inorganic oxide filler.

17. The method of claim 15 wherein the dental composition is a dental restoration.

18. The method of claim 15 wherein the hardenable composition further comprises a photoinitiator and hardening comprises exposing the hardenable dental composition to visible light.

19. A dental article comprising the hardenable dental composition of claim 1 at least partially hardened.

20. A method of treating a tooth surface, the method comprising
providing an at least partially hardened dental article according to claim 19, and
adhering the dental article on a tooth surface in the mouth of a subject.

21. A monomer having the structure

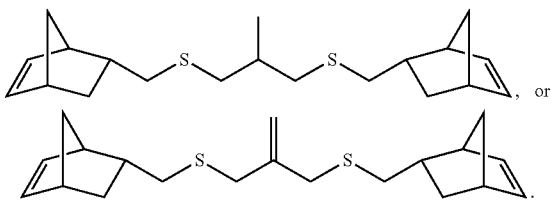

* * * * *

UNITED STATES PATENT AND TRADEMARK OFFICE
CERTIFICATE OF CORRECTION

PATENT NO.       : 8,431,626 B2
APPLICATION NO.  : 13/110898
DATED            : April 30, 2013
INVENTOR(S)      : Christopher Bowman It is certified that error appears in the above-identified patent and that said Letters Patent is hereby corrected as shown below:

In the Specification

Column 2
Line 64, Delete "thereof" and insert -- thereof; --, therefor.
Line 66, Delete "thereof" and insert -- thereof; --, therefor.

Column 3
Line 39, Delete "alkyarylene." and insert -- alkylarylene. --, therefor.

Column 4
Line 52, Delete "norbonene" and insert -- norbornene --, therefor.

Column 5
Line 26, Delete "or and" and insert -- or/and --, therefor.

Column 9
Line 67, Delete "triethlyene" and insert -- triethylene --, therefor.

Column 10
Line 2, Delete "ethylenegylcol" and insert -- ethyleneglycol --, therefor.

Column 11
Line 13, Delete "tetrafluoroboarate." and insert -- tetrafluoroborate. --, therefor.

Column 20
Line 44, Delete "Methacylate" and insert -- Methacrylate --, therefor.

Signed and Sealed this
Twentieth Day of August, 2013

Teresa Stanek Rea
*Acting Director of the United States Patent and Trademark Office*

CERTIFICATE OF CORRECTION (continued)
U.S. Pat. No. 8,431,626 B2

In the Claims

Column 21
Line 60, In Claim 9, delete "triethlyene" and insert -- triethylene --, therefor.

Column 22
Line 46, In Claim 20, after "surface" delete "in the mouth".